United States Patent [19]

Hari

[11] Patent Number: 5,280,121
[45] Date of Patent: Jan. 18, 1994

[54] PERYLENETETRACARBOXYLIC ACID DIIMIDES CONTAINING LONG-CHAIN ALKANOYLAMINO RADICALS

[75] Inventor: Stefan Hari, Reinach, Switzerland

[73] Assignee: Ciba-Geigy Corporation, Ardsley, N.Y.

[21] Appl. No.: 908,504

[22] Filed: Jun. 30, 1992

Related U.S. Application Data

[63] Continuation of Ser. No. 719,857, Jun. 24, 1991, abandoned.

[30] Foreign Application Priority Data

Jun. 27, 1990 [CH] Switzerland ............ 2143/90

[51] Int. Cl.$^5$ ............ C07D 221/18
[52] U.S. Cl. ............ 546/37; 524/90
[58] Field of Search ............ 546/37; 524/90

[56] References Cited

U.S. PATENT DOCUMENTS

| | | | |
|---|---|---|---|
| 2,668,815 | 2/1954 | Nawlasky | 546/37 |
| 3,661,912 | 5/1972 | Kalz et al. | 546/37 |
| 4,238,386 | 12/1980 | Babler | 524/90 |
| 4,262,851 | 4/1981 | Graser et al. | 546/37 |
| 4,379,934 | 4/1983 | Graser et al. | 546/37 |
| 4,978,755 | 12/1990 | Bäbler | 546/37 |

FOREIGN PATENT DOCUMENTS

| | | | |
|---|---|---|---|
| 562588 | 5/1958 | Belgium | 546/37 |
| 283436 | 3/1988 | European Pat. Off. | 546/37 |

OTHER PUBLICATIONS

Sebe et al., Chemical Abstracts, vol. 106, 1987, Abstract 178093c.
Gangneux et al., Chemical Abstracts, vol. 79, 1973, Abstract 92638w.

Primary Examiner—Mukund J. Shah
Assistant Examiner—P. K. Sripada
Attorney, Agent, or Firm—JoAnn Villamizar; George R. Dohmann

[57] ABSTRACT

Compounds of formula

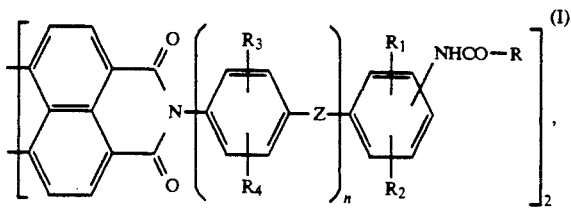

wherein
R is $C_7-C_{21}$alkyl, $C_4-C_{18}$alkenyl, $C_5-C_{12}$cycloalkyl or $C_5-C_6$cycloalkyl-substituted $C_1-C_4$alkyl,
$R_1$, $R_2$, $R_3$ and $R_4$ are each independently of one another hydrogen, chloro, bromo, methyl or methoxy,
Z is a direct bond or —O—, —S—, —NH—, —CO—, —SO$_2$— or —NHCO—, and
n is 0 or 1.

These compounds have excellent suitability as pigments for coloring organic material of high molecular weight, especially polyvinyl chloride, polyolefins and paints.

1 Claim, No Drawings

PERYLENETETRACARBOXYLIC ACID DIIMIDES CONTAINING LONG-CHAIN ALKANOYLAMINO RADICALS

This application is a continuation, of application Ser. No. 719,857, filed Jun. 24, 1991 now abandoned.

The present invention relates to perylenetetracarboxylic acid diimides containing long-chain cyclic or unsaturated alkanoylamino radicals which are attached to both N-atoms through aromatic nuclei, and to the use thereof for colouring organic material of high molecular weight.

N,N'-Dialkylperylene-3,4,9,10-tetracarboxylic acid diimides containing long-chain alkyl radicals for colouring polyolefins are disclosed in U.S. Pat. No. 4,238,386. These compounds are unsatisfactory on the one hand because of their tendency to blooming and, on the other, because their wetfastness properties do not meet all the current requirements of pigment technology.

Perylene-3,4,9,10-tetracarboxylic acid diimides which are substituted at both N-atoms by lower alkanoylamino groups, and the use thereof for colouring paints, coating materials and plastics, are disclosed in U.S. Pat. No. 4,262,851. These pigments too do not meet all of the increasingly stringent requirements for specific applications.

It is disclosed in EP-A 0 283 436 that coloured polyolefins with enhanced properties can be obtained by using perylenetetracarboxylic acid diimides containing long-chain aliphatic radicals which carry carboxyl or carbamoyl groups attached to both N-atoms.

There have now been found novel perylenetetracarboxylic acid diimides which contain long-chain cyclic or unsaturated alkanoylamino radicals attached to both N-atoms through aromatic nuclei and which, surprisingly, colour organic material of high molecular weight in shades of enhanced fastness properties.

Specifically, the invention relates to compounds of formula

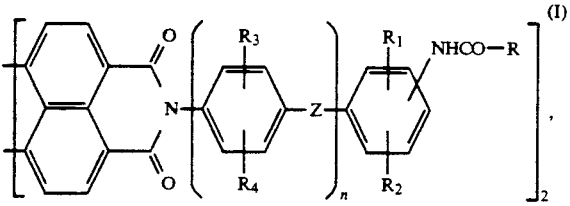

wherein
- R is $C_7$–$C_{21}$alkyl, $C_4$–$C_{18}$alkenyl, $C_5$–$C_{12}$cycloalkyl or $C_5$–$C_6$cycloalkyl-substituted $C_1$–$C_4$alkyl,
- $R_1$, $R_2$, $R_3$ and $R_4$ are each independently of one another hydrogen, chloro, bromo, methyl or methoxy,
- Z is a direct bond or —O—, —S—, —NH—, —CO—, —SO$_2$— or —NHCO—, and
- n is 0 or 1.

R as $C_7$–$C_{21}$alkyl is straight-chain or branched alkyl and is typically n-heptyl, 1-, 2-, 3- or 4-methylhexyl, 1,1- or 3,4-dimethylpentyl, 1- or 3-ethylpentyl, 1,3,3- and 2,4,4-trimethylbutyl, 1-ethyl-3-methylbutyl, 1-propylbutyl, 1-methyl-1-ethylbutyl, 1-propyl-2-methylpropyl, 1-isopropyl-2-methylpropyl, 1,1-diethylpropyl, n-octyl, 2-, 3-, 4-, 5- or 6-methylheptyl, 1,1-dimethylhexyl, 1,5-dimethylhexyl, 1-ethylhexyl, 1-ethyl-2-methylpentyl, 1-ethyl-1-methylpentyl, 1-ethyl-4-methylpentyl, 1-isopropylpentyl, 1,1,3,3-tetramethylbutyl, 2,2,3,3-tetramethylbutyl, 1-isopropyl-3-methylbutyl, nonyl, decyl, 1-neopentyl-3,3-dimethylbutyl, dodecyl, tridecyl, tetradecyl, pentadecyl, hexadecyl, octadecyl, nonadecyl, eicosyl or eneicosyl.

R as $C_4$–$C_{18}$alkenyl may also be straight-chain or branched alkenyl and is typically 1-, 2-or 3-butenyl, 1-methyl-1-propenyl, 1-methyl-2-propenyl, 2-methyl-2-propenyl, 2-methyl-1-propenyl, 1,3-butadienyl, 1-, 2-, 3- or 4-pentenyl, 1-methyl-1-butenyl, 3-methyl-1-butenyl, 3-methyl-2-butenyl, 1,3-pentadienyl, 3-methyl-1,3-butadienyl, 3- or 5-hexenyl, 3-methyl-1-pentenyl, 3-methyl-2-pentenyl, 4-methyl-3-pentenyl, 2-ethyl-1-butenyl, 2-ethyl-2-butenyl, 1- or 6-heptenyl, 1-ethyl-1-pentenyl, 1-ethyl-2-pentenyl, 2,3,3-trimethyl-1-butenyl, 1- or 7-octenyl, 2-methyl-1-octenyl, 2-methyl-2-octenyl, 9-decenyl or 8-heptadecenyl. R as $C_5$–$C_{12}$cycloalkyl may be cyclopentyl, methylcyclopentyl, cyclohexyl, methylcyclohexyl, cycloheptyl, cyclooctyl, cyclodecyl or cyclododecyl.

R as $C_5$–$C_6$cycloalkyl-substituted $C_1$–$C_4$alkyl may be cyclopentylmethyl, cyclohexylmethyl, cyclopentylethyl, cyclohexylpropyl, cyclopentylbutyl or cyclohexylbutyl.

Particularly important compounds of formula I are those wherein n is 0 and, among these, more particularly those compounds wherein $R_1$ and $R_2$ are hydrogen.

Preferred compounds are compounds of formula

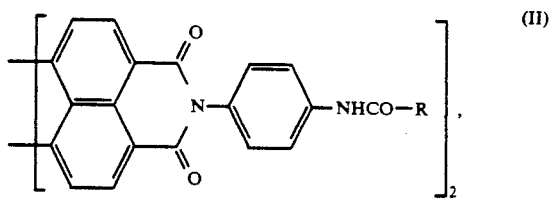

wherein R is $C_{12}$–$C_{18}$alkyl.

The compounds of formula I can be prepared by methods which are commonly known. Conveniently they are obtained in two synthesis steps starting from perylene-3,4,9,10-tetracarboxylic acid or the anhydride thereof, for example by an initial condensation with an amino group of a diamine of formula

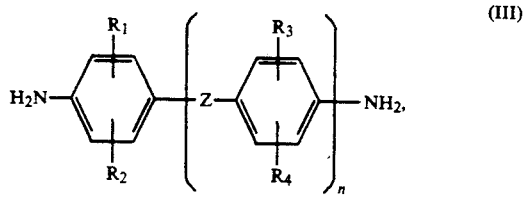

wherein $R_1$, $R_2$, $R_3$, $R_4$ and n are as defined above, and then by a second condensation of the resultant diaminodiimide with a carbonyl chloride of formula

wherein R is as defined above, in accordance with the following reaction scheme:

perylene-3,4,9,10-tetracarboxylic acid or anhydride + at least

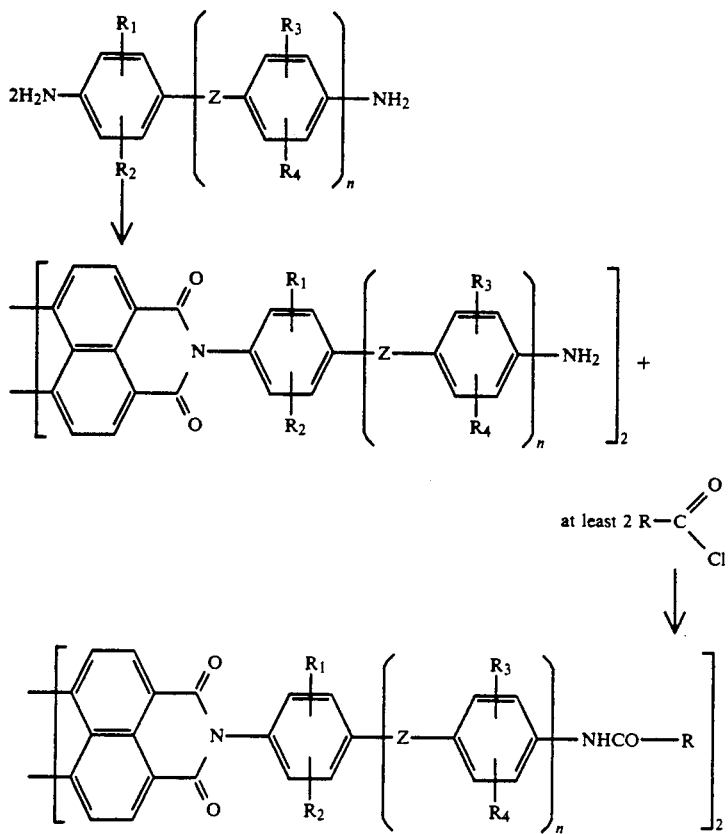

The diaminers of formula III are known compounds, most of which are commercially available.

The carbonyl chlorides of formula IV can be conveniently prepared by known methods from the corresponding known carboxylic acids, most of which are also commercially available, typically by reaction with thionyl chloride. However, it is also possible to react the free acid direct or a lower alkyl ester thereof.

The condensation reactions can be carried out by commonly employed methods, for example in the presence of an organic solvent or, if one of the reactants is used as solvent, under normal or elevated pressure, with or without a catalyst.

Illustrative examples of suitable solvents for the initial condensation to form the corresponding perylene diimides starting from perylene-3,4,9,10-tetracarboxylic acid or the dianhydride thereof are water, dimethyl formamide, N-methylpyrrolidone, quinoline, glycols such as ethylene glycol or propylene glycol, alcohols such as methanol, ethanol, n-propyl alcohol, isopropyl alcohol, n-butyl alcohol and its isomers or diacetone alcohol, as well as aromatic hydrocarbons such as nitrobenzene, chlorobenzene, dichloro- and trichlorobenzenes, toluene and xylenes.

Suitable solvents for the second condensation reaction are typically cyclohexane, aromatic hydrocarbons such as nitrobenzene, chlorobenzene, dichloro- and trichlorobenzenes, toluene, xylenes, cumene and tert-butylbenzene.

If one reactant is used direct as solvent (in excess) in the condensation reactions, then the reaction medium is diluted, after complete amide formation, preferably with one of the organic solvents cited above until the excess component is present in solution. The residual suspension is then filtered, and the excess component can be recovered from the filtrate by evaporation of the solvent.

A further means of preparing the compounds of formula I comprises condensing perylene-3,4,9,10-tetracarboxylic dianhydride in general accordance with the commonly employed methods described above with an amine of formula

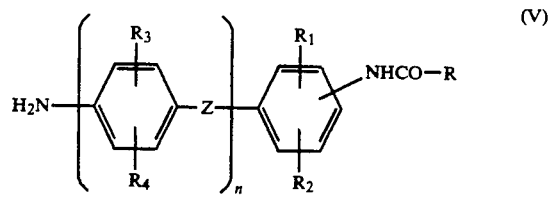

(V)

in the molar ratio 1:2.

The amines of formula V are known or they can be prepared by conventional methods.

The perylene diimides obtained in the practice of this invention are isolated and dried by conventional methods. They have excellent suitability as pigments for colouring organic material of high molecular weight.

Illustrative examples of organic materials of high molecular weight which can be coloured with the pigments of this invention are cellulose ethers and esters, such as ethyl cellulose, nitrocellulose, cellulose acetate or cellulose butyrate, natural resins or synthetic resins, typically polymerisation or condensation resins, such as aminoplasts, preferably urea/formaldehyde and melamine/formaldehyde resins, alkyd resins, phenolic plastics, polycarbonates, polyolefins, polystyrene, polyvinyl chloride, polyamides, polyurethanes, polyesters, ABS, polyphenylene oxides, rubber, casein, silicone and silicone resins, singly or in mixtures.

The above high molecular weight organic compounds may be singly or as mixtures in the form of plastics, melts or of spinning solutions, paints, coating materials or printing inks. Depending on the end use requirement, it is expedient to use the pigments of the invention as toners or in the form of preparations.

The pigments of this invention are especially suitable for mass colouring polyvinyl chloride and, preferably, polyolefins such as polyethylene and polypropylene, as well as for pigmenting paints and coating materials, more particularly automotive lacquers and, among these, preferably metallic paints.

The pigments of the invention can be used in an amount of 0.01 to 30% by weight, preferably 0.1 to 10% by weight, based on the high molecular weight organic material.

The pigmenting of the high molecular weight organic materials with the pigments of this invention is effected conveniently by incorporating the pigments by themselves or in the form of masterbatches in the substrates using roll mills, mixing or milling apparatus. The pigmented material is then brought into the desired final form by methods which are known per se, conveniently by calendering, moulding, extruding, coating, spinning, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after working the pigments into the polymers. To obtain different shades it is also possible to add fillers or other chromophoric components such as white, coloured or black pigments, in any amount to the high molecular weight organic materials.

For pigmenting paints, coating materials and printing inks, the high molecular weight organic materials and the pigments of the invention, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

When used for colouring conveniently e.g. polyvinyl chloride or polyolefins, the pigments of this invention have good general pigment properties, such as good dispersibility, high colour strength and purity, as well as excellent fastness to migration, heat, light and weathering. They have particularly good suitability for pigmenting paints for producing metallic effect finishes. In addition, they have excellent resistance to acid.

The invention is illustrated by the following Examples.

EXAMPLE 1

10 ml of pyridine are added to a mixture of 14.25 g of N,N'-bis(4-aminophenyl)perylenetetracarboxylic acid diimide and 27.75 g of stearoyl chloride in 500 ml of o-dichlorbenzene, and the mixture is heated to 140° C. The dark red suspension is stirred for 6 hours at this temperature and afterwards cooled to 80° C. and filtered. The poduct is washed in succession with 100 ml of o-dichlorobenzene, 1000 ml of hot alcohol and 1000 ml of hot water, and dried at 60° C. in a vacuum drier to give 25.55 g (92.4% of theory) of a red pigment of formula

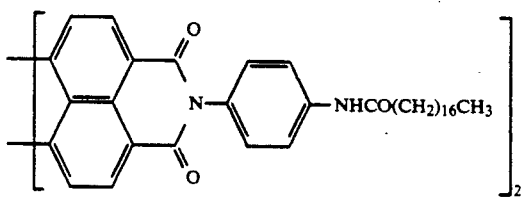

in powder form, which colours polyethylene, polyvinyl chloride and polyamide in strong red shades of excellent fastness to migration, heat and light.

Analysis: cal.: (in %): C 78.23 H 8.02 N 5.07. found: (in %): C 77.86 H 7.84 N 4.84.

EXAMPLES 2-16

Further pigments can be prepared by the method described in Example 1 by acylating each of the diamines listed in column I of the following Table with the acid chloride listed in column II in the molar ratio 1:2. Column III indicates the shade of the PVC sheet coloured with the resultant pigments in accordance with subsequent Example 17.

| Ex. | I | II | III |
|---|---|---|---|
| 2 | N,N'-bis(4-aminophenyl)perylene-tetracarboxylic acid diimide | decanoyl chloride | red |
| 3 | N,N'-bis(4-aminophenyl)perylene-tetracarboxylic acid diimide | 3-cyclopentylpropionyl chloride | orange red |
| 4 | N,N'-bis(4-aminophenyl)perylene-tetracarboxylic acid diimide | lauroyl chloride | red |
| 5 | N,N'-bis(4-aminophenyl)perylene-tetracarboxylic acid diimide | undecanoyl chloride | red |
| 6 | N,N'-bis(4-aminophenyl)perylene-tetracarboxylic acid diimide | tetradecanoyl chloride | red |
| 7 | N,N'-bis(4-aminophenyl)perylene-tetracarboxylic acid diimide | heptanoyl chloride | red |
| 8 | N,N'-bis(4-aminophenyl)perylene-tetracarboxylic acid diimide | octanoyl chloride | red |
| 9 | N,N'-bis(4-aminophenyl)perylene-tetracarboxylic acid diimide | pelargonyl chloride | orange red |
| 10 | N,N'-bis(4-aminophenyl)perylene-tetracarboxylic acid diimide | palmitoyl chloride | red |
| 11 | N,N'-bis(4-aminophenyl)perylene-tetracarboxylic acid diimide | 10-undecenoyl chloride | dark red |
| 12 | N,N'-bis(4-aminophenyl)perylene-tetracarboxylic acid diimide | oleyl chloride | red |
| 13 | N,N'-bis(2,5-dimethyl-4-aminophenyl)perylenetetracarboxylic acid diimide | stearoyl chloride | orange |
| 14 | N,N'-bis(2,5-dimethyl-4-aminophenyl)perylenetetracarboxylic acid diimid | lauroyl chloride | orange |
| 15 | N,N'-bis(2,5-dimethyl-4-aminopheynyl)perylenetetracarboxylic acid diimide | oleyl chloride | orange |
| 16 | N,N'-bis(3-aminophenyl)perylene-tetracarboxylic acid diimide | lauroyl chloride | red |

EXAMPLE 17

40 mg of the perylene diimide pigment according to Example 1, 7.3 ml of dioctyl phthalate and 13.3 g of stabilised polyvinyl chloride ®LONZA E-722 are thoroughly mixed in a glass beaker with a glass rod, and the mixture is processed to a thin sheet on a roll mill for 5 minutes at 160° C. The PVC sheet so obtained is coloured in a strong red shade of high purity and very good lightfastness. The dispersibility of the pigment is excellent.

EXAMPLE 18

A mixture of 1.0 g of the perylene diimide pigment obtained according to Example 1, 1.0 g of antioxidant ®IRGANOX 1010 (CIBA-GEIGY AG) and 1000 g of HD polyethylene granules (®VESTOLEN A60-16, HUELS) is stirred for 15 minutes in a 3 liter glass bottle on a roller gear table. The mixture is then extruded in two passes in a single screw extruder. The granulate so obtained is moulded to boards at 250° C. in an injection moulding machine (®Allround Aarburg 200) for 5 minutes. The mouldings are coloured in a strong, level red shade of high purity and excellent lightfastness.

EXAMPLE 19

1000 g of polypropylene granules (®DAPLEN PT-55, Chemie LINZ) and 1.0 g of the perylene diimide pigment obtained according to Example 1 are mixed for 15 minutes in a 3 liter bottle on a roller gear bed. The mixture is subsequently extruded twice through a single-screw extruder and then granulated. The granules so obtained are spun at 280°–285° C. by the melt spinning process. The red filaments have very good lightfastness and excellent textile properties, such as rubfastness and wetfastness to detergents and solvents. The pigment has excellent heat resistance during the spinning process at 285° C.

EXAMPLE 20

The process described in Example 18 is repeated, but using, in addition to the coloured pigment, 10 g of titanium dioxide ®KRONOS RN-57-P (KRONOS Titan GmbH), to give red pressed sheets having comparably good heat resistance. The pressed sheets, which are injection moulded at 200°–280° C., exhibit no colour deviations after cooling.

EXAMPLE 21

A mixture of
130 g of steatite balls ($\phi=8$ mm),
45.5 g of a thermosetting acrylic varnish consisting of
  41.3 g of acrylic resin ®VIACRYL VC 373, 60% (VIANOVA Kunstharz AG),
  16.3 g of melamine resin ®MAPRENAL TTX, 55% (HOECHST AG),
  32.8 g of xylene,
  4.6 g of ethyl glycol acetate,
  2.0 g of butyl acetate and
  1.0 g of ®silicone oil A, 1% in xylene (BAYER AG), and
2.5 g of the perylene diimide obtained in Example 1
is dispersed in a 200 ml glass bottle with twist-off stopper for 72 hours on a roller gear bed. The steatite balls are removed and then 8.0 g of the dispersed masstone mixture, 0.6 g of aluminium paste ®ALCOA, (60–65% Al content, Aluminium Corp. of America), 1.0 g of methyl ethyl ketone and 18.4 g of the above thermosetting acrylic varnish are thoroughly mixed, and the mixture is sprayed on to aluminium sheets and subsequently baked for 30 minutes at 130° C., to give very strong red metallic effect finishes of excellent fastness properties.

What is claimed is:

1. A compound of formula

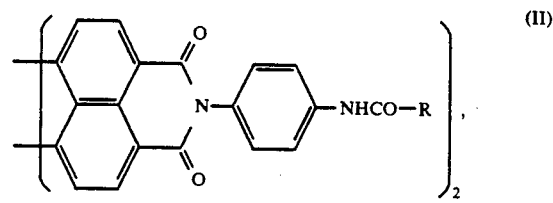

(II)

wherein R is $C_{12}$–$C_{18}$alkyl.

* * * * *